US008211668B2

(12) United States Patent
Patkar et al.

(10) Patent No.: US 8,211,668 B2

(45) Date of Patent: Jul. 3, 2012

(54) APPARATUS AND METHODS FOR OSMOTICALLY SHOCKING CELLS

(75) Inventors: Anant Y. Patkar, San Diego, CA (US); Subrata Sen, San Diego, CA (US); Micheal L. Chappell, Lake Jackson, TX (US)

(73) Assignee: Dow AgroSciences, LLC., Indianapolis, IN (US)

( * ) Notice: Subject to any disclaimer, the term of this patent is extended or adjusted under 35 U.S.C. 154(b) by 585 days.

(21) Appl. No.: 12/013,042

(22) Filed: Jan. 11, 2008

(65) Prior Publication Data

US 2008/0182295 A1 Jul. 31, 2008

Related U.S. Application Data

(60) Provisional application No. 60/880,195, filed on Jan. 12, 2007.

(51) Int. Cl.

| | |
|---|---|
| ***C12P 21/04*** | (2006.01) |
| ***C12M 1/00*** | (2006.01) |
| ***C12N 5/04*** | (2006.01) |

(52) U.S. Cl. .... 435/69.1; 435/244; 435/419; 435/289.1; 435/375

(58) Field of Classification Search ........................ None
See application file for complete search history.

(56) References Cited

FOREIGN PATENT DOCUMENTS

WO WO2005017174 A2 2/2005

OTHER PUBLICATIONS

French et al. Development of simple method for recovery of recombinant proteins from the *Escherichia coli* periplasm (Enzyme and Microbial Technology 19:332-338, 1996.*

Davidson et al Lysozyme-Osmotic Shock method for localization of periplasmic redox proteins in bacteria 2002 Methods in Enzymology, vol. 353, pp. 121-130.*

Optimization of an Osmotic Shock Procedure for Isolation of a Protein Product Expressed in *E. coli* Anurag S. Rathore Biotechnolol. Prog. 2003 p. 1541-46.*

Lysozyme-Osmotic shock methods for localization of Periplasmic Redox Proteins in Bacteria Davidson et al. methods in Enzymology vol. 353, 2002, p. 121-130.*

Large scale recovery and purification of periplasmic recombinant protein from *E. coli* using expanded bed adsorption chromatography followed by new ion exchange media Journal of Biotechnology1996, vol. 48, 9-14.*

Continuous culture—making a comeback? Paul A. Hoskisson Microbiology, 2005, 151, 3153-59.*

Rathore, Anurag S., et al., Optimization of an Osmotic Shock Procedure for Isolation of a Protein Product Expressed in *E. coli*, Biotechnol. Prog., Aug. 20, 2003, pp. 1541-1546, vol. 19, American Chemical Society, Washington, D.C.

Neu, Harold C., et al., The Release of Enzymes From *Escherichia coli* by Osmotic Shock and During the Formation of Spheroplasts, J. Biol. Chem., Sep. 1965, pp. 3685-3692, vol. 240, No. 9.

Nossal, Nancy G., et al., The Release of Enzymes by Osmotic Shock From *Escherichia coli* in Exponential Phase, J. of Biol. Chem., Jul. 1966, pp. 3055-3062, vol. 241, No. 13.

* cited by examiner

*Primary Examiner* — Kagnew H Gebreyesus

(74) *Attorney, Agent, or Firm* — Jarett K. Abramson; Traskbritt, P.C.

(57) ABSTRACT

A method of preparing a recombinant polypeptide of interest includes fermenting a host cell being transformed with a recombinant expression system capable of bringing about secretion of a polypeptide of interest into the periplasm of said host cell. The polypeptide of interest is extracted from the periplasm by applying a continuous osmotic shock to the host cells contained in a fermentation medium. An apparatus for osmotically shocking cells includes a first reservoir containing cells in a first solution and a second reservoir containing a second solution, the first solution having a higher osmolarity than the second solution. A method for osmotically shocking cells using the first and second solutions is also disclosed. Also disclosed is a method of isolating a recombinant polypeptide of interest from a cell.

28 Claims, 2 Drawing Sheets

APPARATUS AND METHODS FOR OSMOTICALLY SHOCKING CELLS

CROSS-REFERENCE TO RELATED APPLICATION

This application claims the benefit of U.S. Provisional application No. 60/880,195, filed Jan. 12, 2007, entitled "APPARATUS AND METHODS FOR OSMOTICALLY SHOCKING CELLS", the disclosure of which is being incorporated by reference.

FIELD OF THE INVENTION

The present invention related generally to the field of biotechnology. More specifically, the present invention relates to apparatus and methods for the isolation of molecules from the periplasm of a cell.

BACKGROUND OF THE INVENTION

In a number of commercial bioprocesses, mechanical cell disruption is used to release intracellular contents. This procedure releases all intracellular contents resulting in significant challenges in further downstream unit operations. For protein molecules in the periplasmic space of bacteria, a lab scale batch osmotic shock procedure has been used to selectively release the periplasmic contents without complete cell disruption. Such a process typically begins by equilibrating fermentation broth with high molarity salt or sugar solution (soak buffer) to build high osmotic pressure within the cells. This is followed by mixing with low osmolarity buffer (shock buffer) in a batch mode for a finite period of time for release of the periplasmic contents. Release is followed by removal of the cells by centrifugation. This traditional batch process is time consuming and has other limitations, such as difficulty in scaling up, accurate control of exposure time, and low throughput. These factors limit its applicability for the large scale release of molecules of interest. As such, methods and apparatus that overcome these limitations would be an improvement in the art.

BRIEF SUMMARY OF THE INVENTION

In one embodiment of the invention, a method of preparing a recombinant polypeptide of interest includes fermenting a host cell being transformed with a recombinant expression system capable of bringing about secretion of a polypeptide of interest into the periplasm of said host cell. The fermentation is performed in a fermentation medium under conditions such that the polypeptide of interest is secreted into the periplasm of the host cell. The polypeptide of interest is extracted from the periplasm by applying a continuous osmotic shock to the host cells contained in the fermentation medium.

In one embodiment of the invention, an apparatus for osmotically shocking cells is disclosed. The apparatus can include a first reservoir containing cells in a first solution and a second reservoir containing a second solution. The first solution can have a higher osmolarity than the second solution. The apparatus can further include a means for generating a first fluid stream comprising the first solution, a means for generating a second fluid stream comprising the second solution, and a means for combining the first and second fluid streams into a third fluid stream.

In another embodiment, a method for osmotically shocking cells is disclosed. The method can include providing a first solution comprising cells and a second solution. The osmolarity of the first solution can be higher than the osmolarity of the second solution. The method can further include generating a first fluid stream comprising the first solution, generating a second fluid stream comprising the second solution, and combining the first and second fluid streams into a third fluid stream.

In yet another embodiment, a method of isolating a recombinant polypeptide of interest from a cell is disclosed. The method can include providing a first solution comprising a cell producing the polypeptide of interest. The cell secretes the polypeptide of interest into the periplasmic space of the cell. The method can further include providing a second solution wherein the osmolarity of the first solution is higher that the osmolarity of the second solution. The method can further include generating a first fluid stream comprising the first solution, generating a second fluid stream comprising the second solution, combining the first and second fluid streams into a third fluid stream, and releasing into the third fluid stream the recombinant polypeptide of interest from the periplasm of the cell. The cell can then be removed from the third fluid stream.

BRIEF DESCRIPTION OF THE DRAWINGS

It will be appreciated by those of ordinary skill in the art that the elements depicted in the various drawings are not to scale, but are for illustrative purposes only. The nature of the presenting invention, as well as example embodiments of the present invention, may be more clearly understood by reference to the following detailed description of the invention, to the appended claims, and to the several drawings, in which:

DETAILED DESCRIPTION OF THE INVENTION

The present invention relates to apparatus and methods for subjecting cells to osmotic shock. The present invention further relates to methods and apparatus for the preparation of recombinant peptides through the use of osmotic shock. It will be apparent to those of ordinary skill in the art that the embodiments described herein, while illustrative, are not intended to so limit the invention or the scope of the appended claims. Those of ordinary skill in the art will understand that various combinations or modifications of the embodiments presented herein may be made without departing from the scope of the present invention.

According to one embodiment of the invention, a method of preparing a recombinant polypeptide of interest includes fermenting a host cell being transformed with a recombinant expression system capable of bringing about secretion of a polypeptide of interest into the periplasm of the host cell. The fermentation is performed in a fermentation medium under conditions such that the polypeptide of interest is secreted into the periplasm of the host cell. The polypeptide of interest can be selected from the group consisting of an interferon, an interleukin, a growth hormone, a growth factor, a cytokine, an enzyme, an enzyme inhibitor, an antibody and an antibody fragment. The polypeptide of interest is extracted from the periplasm by applying a continuous osmotic shock to the host cells contained in the fermentation medium. According to a particular embodiment, applying a continuous osmotic shock to the host cells includes providing a first solution comprising cells, and providing a second solution, wherein the osmolarity of the first solution is higher that the osmolarity of the second solution. A first fluid stream that includes the first solution is generated and a second fluid stream that includes said second solution is generated. The first and second fluid streams are then combined into a third fluid stream. The continuous osmotic shock can be accomplished by continuous mixing of a high molarity slurry with a low molarity shock buffer. The high molarity slurry can be selected, for example, from the group consisting of a high sugar or salt concentration. The low molarity shock buffer can be selected, for example, from the group consisting of Tris, Bis-Tris and phosphate. The method can optionally also include administering a heat exchanger after or before osmotic pressure is released from the cells, administering a solvent before or after osmotic pressure is released from the cells, and administering a chemical treatment before or after osmotic pressure is released from the cells.

Figure 1:
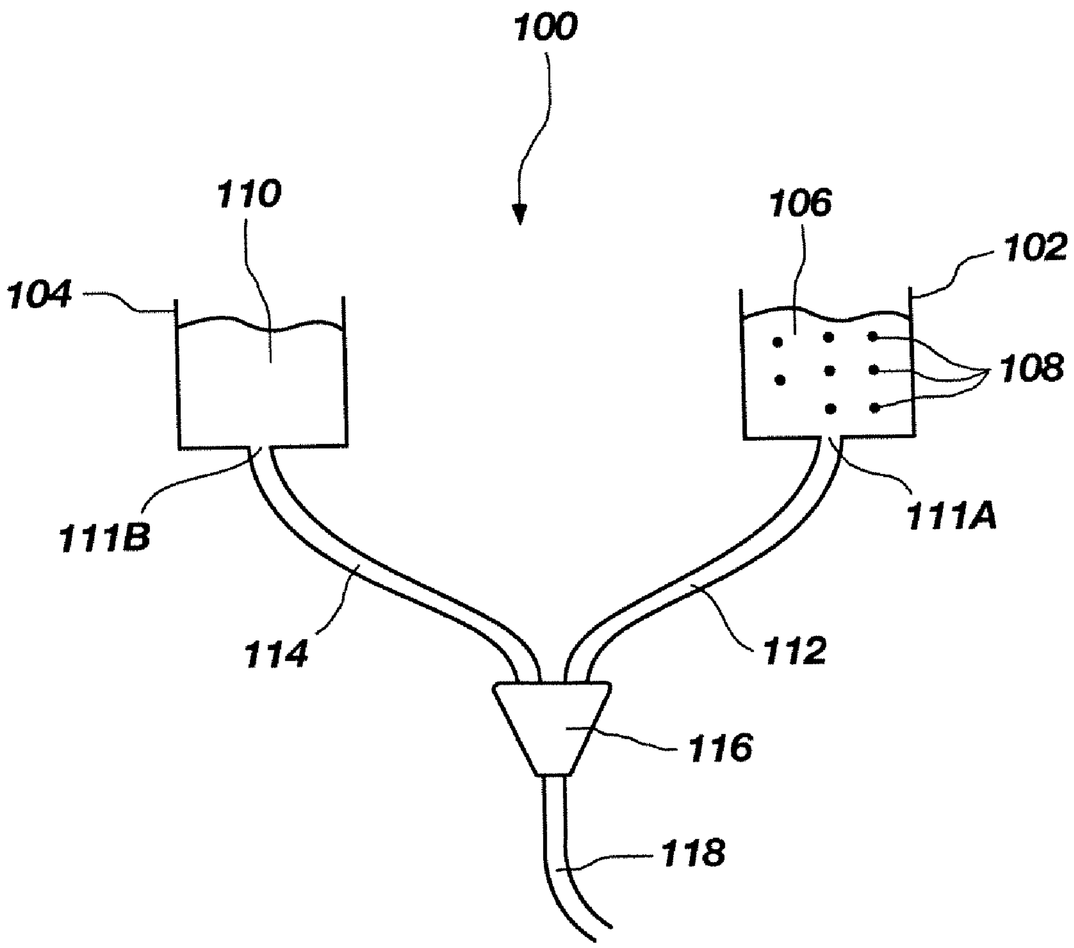
FIG. 1 is a schematic diagram of an example apparatus for osmotically shocking cells.

Referring to FIG. 1, there is illustrated a schematic view of an example embodiment of an apparatus 100 for osmotically shocking cells according to the present invention. As illustrated, the apparatus 100 includes a first reservoir 102 containing a first solution 106. Depicted in first solution 106 are cells 108. The apparatus 100 further includes a second reservoir 104 containing a second solution 110. Depicted in the bottoms of first reservoir 102 and second reservoirs 104 are means for generating a fluid streams 111A and 111B. Means for generating a first fluid stream 111A generates first fluid stream 112 comprising first solution 106 and cells 108. Means for generating a fluid stream 111B generates second fluid stream 114 comprising second solution 110. Further depicted is a means for combining fluid streams 116 that combines first fluid stream 112 and second fluid stream 114 to form third fluid stream 118.

Although means for generating a fluid stream 111A and 111B are depicted as a holes in first and second reservoirs 102 and 104, any means for generating a fluid stream known to one of ordinary skill in the art may be used. Examples of means for generating a fluid stream 111A and 111B include, but are not limited to, holes, spigots, spouts, valves, pouring, tubing, pumps, and combinations thereof.

As will be apparent to one of ordinary skill in the art, means for combining fluid streams 116 may be any apparatus or device that can combine first fluid stream 112 and second fluid stream 114 to form third fluid stream 118. Examples of suitable means for combining fluid streams 116 that may be used in example embodiments of the present invention include, but are not limited to, T-joints, Y-joints, and funnels. In a particular embodiment, the means for combining fluid streams 116 can be an apparatus or device that does not allow for prolonged retention of the combination of first fluid stream 112 and second fluid stream 114 before the formation third fluid stream 118. In a particular embodiment, first solution 106 and second solution 110 can be combined at a 1:4 ratio.

In another embodiment, first solution 106 can have a higher osmolarity than second solution 110. First solution 106 can have a solute concentration of from about 0.5 M to about 10 M. First solution 106 can have a solute concentration, for example, of from about 2 M to about 6 M and, more specifically, can have a solute concentration of from about 1 M to about 3 M.

Second solution 110 can have a solute concentration of from about 0 M to about 1 M and, more specifically, a solute concentration of from about 0 M to about 0.5 M, or a solute concentration of from about 0 M to about 0.1 M.

Examples of solutes that may be useful as components of first solution 106 and second solution 110 include, but are not limited to, sugars, salts, glucose, sucrose, glycerol, sodium chloride, sodium sulfate, sodium phosphate, sodium nitrate, potassium chloride, potassium sulfate, potassium phosphate, potassium nitrate, magnesium chloride, magnesium sulfate, magnesium phosphate, magnesium nitrate, calcium chloride, calcium sulfate, calcium phosphate, calcium nitrate, ammonium sulfate, and combinations thereof. In particular embodiments, first solution 106 and second solution 110 include glycerol and/or sodium chloride.

As will be appreciated by one of ordinary skill in the art, cells 108 can be any kind of biological cells that one wishes to subject to osmotic shock. Examples of cell types that may be osmotically shocked include, but are not limited to, microbial cells, bacterial cells, yeast cells, mammalian cells, insect cells, animal cells, plant cells, *Pseudomonas* sp., *E. coli, Klebsialla* sp., *Saccharomyces* sp., *Pichia* sp., and *Hansenuela* sp. Cells 108 can include a periplasmic space and can also produce a molecule of interest. In particular embodiments, the molecule of interest can be a polypeptide and cells 108 can produce a polypeptide of interest that is localized to the periplasmic space. Representative polypeptides of interest can be selected, for example, from the group consisting of an interferon, an interleukin, a growth hormone, a growth factor, a cytokine, an enzyme, an enzyme inhibitor, an antibody and an antibody fragment.

In normal operation of a particular embodiment of the invention, reservoir 102 contains a first solution 106 comprising cells 108. Reservoir 104 contains second solution 110, which is of lower osmolarity than first solution 106. Means for generating a fluid stream 111A generates first fluid stream 112, which includes first solution 106 and cells 108. Means for generating a fluid stream 111B generates second fluid stream 114, which includes second solution 110. First fluid stream 112 and second fluid stream 114 are brought into fluid communication with each other to generate third fluid stream 118. For example, first fluid stream 112 and second fluid stream 114 may be combined using a means for combining fluid streams 116 to form third fluid stream 118.

Figure 2:
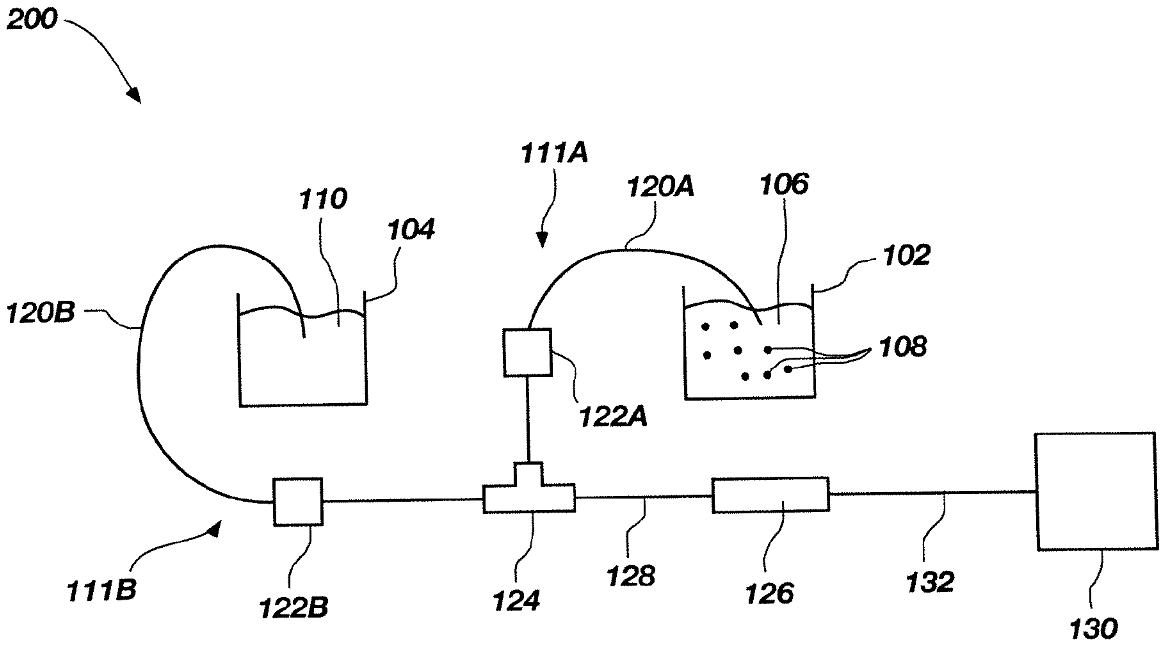
FIG. 2 is a schematic diagram of a further example apparatus for osmotically shocking cells.

Referring to FIG. 2, there is illustrated a schematic view of an example embodiment of an apparatus 200 for osmotically shocking cells according to the present. As can be seen therein, apparatus 200 has some of the same features as apparatus 100. Means for generating a fluid stream 111A includes pump 122A and tubing 120A that is inserted into the first solution 106. Pump 122A and tubing 120A together generate first fluid stream 112 (not depicted in FIG. 2) which flows through tubing 120A. Means for generating a fluid stream 111B comprises pump 122B and tubing 120B that is inserted into the second solution 110. Pump 122B and tubing 120B together generate second fluid stream 114 (not depicted) which flows through tubing 120B. Pumps 122A and B may separately and variably control the rate at which each of first fluid stream 112 and/or second fluid stream 114 flow through tubings 120A and 120B. Tubings 120A and 120B are fluidly connected to T-joint 124. T-joint 124 is connected to mixer 126 via tubing 128. Mixer 126 is connected to clarifier 130 via tubing 132.

As will be appreciated by one of ordinary skill in the art, tubings 120A and 120B, 128, and 132 may be any sort of device or material for directing a fluid stream. Examples of items that are suitable for use as tubing 120A and B, 128, and 132 include, but are not limited to, channels, piping, tubing, rubber tubing, tygon tubing, and combinations thereof.

Pumps 122A and B may be any sort of pump useful for moving a fluid stream. Examples of pumps 122A and B that may be useful in embodiments according to the present invention include, but are not limited to, peristaltic pumps, hose pumps, metering pumps, gear pumps, helical pumps, magnetic drive pumps, rotodynamic pumps, positive displacement pumps, jet pumps, gas lift pumps, electromagnetic pumps, eductor-jet pumps, rotary pumps, rotary vane pumps, reciprocating pumps, and diaphragm pumps. In a particular embodiment, pumps 122A and 120B provide first solution 106 and second solution 110 to T-joint 124 at a 1:4 ratio, and first solution 106 and second solution 110 are provided to T-joint 124 in the orientation depicted in FIG. 2.

Mixer 126 may be any type of mixer useful for mixing the contents of a fluid. Examples of mixers 126 that may be useful in embodiments according to the present invention include, but are not limited to, dispersers, high shear mixers, multi-shaft mixers, planetary mixers, ribbon-paddle mixers, vertical blenders, and static mixers. Use of a static mixer can provide an effective device to mix streams of dissimilar physical and flow attributes. Static mixers have no moving parts, thus creating relatively low shear and providing an effective control of contact/residence time within the device.

Clarifier 130 may be any type of device useful for the separation of contents of a fluid based upon size or density. Examples of clarifiers 130 that may be useful in embodiments according to the present invention include, but are not limited to, filters, centrifuges, microfilters, tangential flow microfilters, continuous centrifuges, and disc stack continuous centrifuges. Currently preferred is a disc stack continuous centrifuge.

In addition, embodiments of an apparatus according to the present invention may comprise a heat exchanger or other temperature altering device to alter the temperature of one or both of first solution 106 and second solution 110 and/or one or more of first fluid stream 112, second fluid stream 114, and third fluid stream 118. As will be apparent to one of ordinary skill in the art, a heat exchanger or other temperature-altering device may be placed anywhere in the apparatus in order to alter the temperature of one or both of first solution 106 and/or second solution 110 and/or one or more of first, second, and third fluid streams 112, 114, and 118 at that location. Non-limiting examples for the placement of a heat exchanger or other temperature-altering devices include between T-joint 124 and mixer 126, between mixer 126 and clarifier 130, and in one or both of the reservoirs 102 and 104. Examples of suitable heat exchangers or other temperature-altering devices that may be used in embodiments of the present invention include, but are not limited to, electric heaters, cooling or heating blankets, cooling or heating jackets, shell heat exchangers, tube heat exchangers, plate heat exchangers, plate-and-frame heat exchangers, regenerative heat exchangers, dynamic heat exchangers, scraped surface heat exchangers, adiabatic wheel heat exchangers, and heat pumps.

In addition, an embodiment of an apparatus according to the present invention may comprise access ports or devices where desired. Such access ports or devices would allow the addition of further components or chemicals to one or both of first and second solutions 106 and 110 and/or one or more of first, second, and third fluid streams 112, 114, and 118 at any point. Examples of suitable access ports or, devices that may be used in the present invention include, but are not limited to, doors, ports, diaphragms, valves, junctions, and combinations thereof.

In normal operation, the apparatus depicted in FIG. 2 draws the first solution 106 containing cells 108 through tubing 120A using pump 122A and delivers the first solution 106 to T-joint 124. Second solution 110 is also drawn through tubing 120B using pump 122B and delivered to T-joint 124. First solution 106, cells 108, and second solution 110 are combined within T-joint 124. Cells 108 are subjected to osmotic shock by virtue of the combination of first solution 106 and second solution 110 and the osmotic shock causes the release of molecules in the periplasmic space of the cells into the surrounding solution. The solution resulting from the combination of first solution 106, cells 108, and second solution 110 is passed through mixer 126 and onto clarifier 130.

An example embodiment of the present invention provides for a method of isolating a recombinant polypeptide of interest. The method includes growing or fermenting a cell producing a recombinant polypeptide of interest, the cell secreting the recombinant polypeptide of interest into the periplasm of the cell. The cells are incubated in a high osmolarity solution. A fluid stream of the cells in the high osmolarity solution are combined with a fluid stream of a low osmolarity solution to form a new fluid stream, wherein the mixing of the cells in the high osmolarity solution with a fluid stream of a low osmolarity solution causes the cells to release the recombinant polypeptide of interest into the new fluid stream. The new fluid stream may then be mixed, (e.g., with a static mixer) and the cells then are separated from the new fluid stream containing the recombinant polypeptide of interest using a clarifying device, such as a filter or a centrifuge.

As will be apparent to one of skill in the art, the cell may naturally express the polypeptide of interest and secrete it into the periplasmic space, or the cell can be engineered to contain a construct, which may be integrated into the genome, to produce the polypeptide of interest and secrete it into the periplasmic space.

The present invention is further described in the following examples, which are offered by way of illustration and are not intended to limit the invention in any manner.

EXAMPLES

Example 1

Osmotic Shock by Combination of Fluid Streams

A *Pseudomonas fluorescences* bacterial strain (DC 456) expressing human growth hormone (hGH) in the periplasmic space was used. After fermentation at 20 L bioreactor scale, the broth was centrifuged in a laboratory batch centrifuge. The cell paste (3811 g) was mixed with 3.5 L of soak buffer (25% sucrose pH 7.2) for 30 min. The shock buffer consisted of 20 mM Tris, pH 7.2). The setup for osmotic shock by combination of fluid streams consisted of two peristaltic pumps (Masterflex L/S, Model #77200-62) for continuously flowing two streams (equilibrated cell slurry and shock buffer), which were combined using a T-joint, followed by a static mixer (Conprotec, FM 08-10-36) for rapid mixing of the two streams, attached to a continuous disc stack centrifuge (Westfalia SC-6) for separation of the cells from the liquid extract. The flow rates for the equilibrated cell slurry and the shock buffers were 200 mL/min and 800 mL/min, respectively. The amounts of hGH in the samples from the feed and extract streams were measured by capillary electrophoresis (caliper LabChip 90). The step yield for this process (amount of hGH in the extract divided by that in the fermentation broth) was about 70%.

Example 2

Osmotic Shock by Batch Processing

A *Pseudomonas fluoresescens* bacterial strain (DC 456) expressing human growth hormone (hGH) in the periplasmic space was used. After fermentation at 20 L bioreactor scale, the broth was centrifuged in a laboratory batch centrifuge.

The cell paste (150-225 g) was mixed with 150-225 g of soak buffer (25% sucrose with 20 mM Bis-Tris, pH 7.2) for 30 min. The equilibrated slurry was mixed with 4× volume of shock buffer (20 mM Bis-Tris, pH 7.2), held for 30 minutes, and centrifuged in a laboratory batch centrifuge (Eppendorf). The amounts of hGH in the samples from the feed and extract streams were measured by capillary electrophoresis (caliper LabChip 90). The step yield for this process (amount of hGH in the extract divided by that in the fermentation broth) was about 40%.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of preparing a recombinant polypeptide of interest, comprising:

fermenting in a fermentation medium a host cell transformed with a recombinant expression system where a polypeptide of interest is secreted into the periplasm of the cell, and wherein a fermentation broth is formed;

providing a solution;

admixing the solution with the cell to form a high molarity slurry;

providing a low molarity shock buffer, wherein the osmolarity of the high molarity slurry is higher than the osmolarity of the low molarity shock buffer;

generating a first fluid stream comprising the high molarity slurry, wherein the first fluid stream has a first flow rate;

generating a second fluid stream comprising the low molarity shock buffer, wherein the second fluid stream has a second flow rate;

continuously combining the first and second fluid streams into a third fluid stream, wherein the second flow rate is greater than the first flow rate; and extracting the polypeptide of interest from the third fluid stream, wherein a polypeptide extract having at least 70% of the polypeptide of interest compared to the fomentation broth is formed.

2. The method according claim 1, wherein the solution is selected from the group consisting of a high sugar or salt concentration.

3. The method according to claim 1, wherein the low molarity shock buffer has a pH of from about 5 to about 9.

4. The method according to claim 1, further comprising administering a heat exchanger before or after osmotic pressure is released from the cells.

5. The method according to claim 1, further comprising administering a solvent before or after osmotic pressure is released from the cells.

6. The method according to claim 1, further comprising administering a chemical treatment before or after osmotic pressure is released from the cells.

7. A method of osmotically shocking cells, the method comprising:

providing a first solution comprising cells;

providing a second solution;

wherein the osmolarity of said first solution is higher that the osmolarity of said second solution;

generating a first fluid stream having a first flow rate comprising said first solution;

generating a second fluid stream having a second flow rate comprising said second solution; and continuously combining said first and second fluid streams into a third fluid stream wherein the second flow rate is greater than the first flow rate, wherein proteins in the periplasmic space of the cells are released with a yield that is about 30% greater than the proteins are released from cells osmotically shocked by batch processing.

8. The method according to claim 7, wherein said cells are selected from the group consisting of microbial cells, plant cells, fungi cells, bacterial cells, mammalian cells, and yeast cells.

9. The method according to claim 7, wherein said cells are selected from the group consisting of *Pseudomonas* sp., *E. coli, Klebslalla* sp., *Saccharomyces* sp., *Pichia* sp., and *Hansenuela* sp.

10. The method according to claim 7, wherein said cells have a periplasmic space and wherein said cells produce a protein of interest.

11. The method according to claim 7, wherein said first solution comprises a first solute set present in said first solution in a molarity from about 0.5 M to about 10 M; wherein said first solute set comprises at least one solute.

12. The method according to claim 7, wherein said second solution comprises a second solute set present in said second solution in a molarity from about 0 M to about 1 M; wherein said second solute set comprises at least one solute.

13. The method according to claim 11, wherein said first solute set or said second solute set comprises a sugar or a salt.

14. The method according to claim 13, wherein said sugar or said salt is selected from the group consisting of glucose, sucrose, glycerol, sodium chloride, sodium sulfate, sodium phosphate, sodium nitrate, potassium chloride, potassium sulfate, potassium phosphate, potassium nitrate, magnesium chloride, magnesium sulfate, magnesium phosphate, magnesium nitrate, calcium chloride, calcium sulfate, calcium phosphate, calcium nitrate ammonium sulfate, and combinations thereof.

15. The method according to claim 7, wherein said continuous combining said first and second fluid streams into said third fluid stream comprises:

defining a first fluid path along the path of said first fluid stream;

defining a second fluid path at about a right angle to said first path that intersects with said first fluid path and does not continue past said first fluid path to form an intersection of said first and second fluid paths;

defining a third fluid path connected to said intersection of said first and second flow paths wherein said third fluid path and said first fluid path form a substantially straight flow path;

providing said first solution to said second fluid path;

providing said second solution to said first fluid path; and combining said first and second solutions at said intersection of said first and said second flow path such that said third fluid stream exits from said third fluid path.

16. The method according to claim 15, further comprising mixing said third fluid stream with a static mixer.

17. The method according to claim 7, wherein said cell produces a polypeptide of interest and secretes said polypeptide of interest into the periplasmic space of said cell.

18. The method according to claim 1, wherein the host cell is selected from the group consisting of microbial cells, plant cells, fungi cells, bacterial cells, mammalian cells, and yeast cells.

19. The method according to claim 18, wherein the host cell is selected from the group consisting of *Pseudomonas* sp., *E. coli, Klebsialla* sp., *Saccharomyces* sp., *Pichia* sp., and *Hansenuela* sp.

20. The method according to claim 1, wherein the solution comprises a solute set present in a molarity from about 0.5 M to about 10 M, and wherein the solute set comprises at least one solute.

21. The method according to claim 1, wherein the low molarity shock buffer comprises a solute set present in a molarity from about 0 M to about 1 M, and wherein the solute set comprises at least one solute.

22. The method according to claim 20, wherein the solute set comprises a sugar or a salt.

23. The method according to claim 21, wherein the solute set comprises a sugar or a salt.

24. The method according to claim 22, wherein the sugar or salt is selected from the group consisting of glucose, sucrose, glycerol, sodium chloride, sodium sulfate, sodium phosphate, sodium nitrate, potassium chloride, potassium sulfate, potassium phosphate, potassium nitrate, magnesium chloride, magnesium sulfate, magnesium phosphate, magnesium nitrate, calcium chloride, calcium sulfate, calcium phosphate, calcium nitrate ammonium sulfate, and combinations thereof.

25. The method according to claim 23, wherein the sugar or salt is selected from the group consisting of glucose, sucrose, glycerol, sodium chloride, sodium sulfate, sodium phosphate, sodium nitrate, potassium chloride, potassium sulfate, potassium phosphate, potassium nitrate, magnesium chloride, magnesium sulfate, magnesium phosphate, magnesium nitrate, calcium chloride, calcium sulfate, calcium phosphate, calcium nitrate ammonium sulfate, and combinations thereof.

26. The method according to claim 1, further comprising mixing the third fluid stream with a static mixer.

27. A method of isolating a polypeptide of interest, comprising:

providing a slurry comprising a cell having been fermented in a fermentation medium, wherein the periplasm of the cell comprises a polypeptide of interest;

providing a shock buffer, wherein the osmolarity of the slurry is higher than the osmolarity of the shock buffer;

generating a first fluid stream comprising the slurry, wherein the first fluid stream has a first flow rate;

generating a second fluid stream comprising the shock buffer, wherein the second fluid stream has a second flow rate that is greater than the first flow rate;

defining a first fluid path along the path of the second fluid stream;

defining a second fluid path that intersects with the first fluid path to form an intersection of the first and second fluid paths;

defining a third fluid path connected to the intersection of the first and second fluid paths;

providing the first fluid stream through the first fluid path;

providing the second fluid stream through the second fluid path;

continuously combining the first and second fluid streams at the intersection of the first and said second fluid paths, such that a third fluid stream comprising the combined first and second fluid streams exits the intersection of the first and second fluid paths through the third fluid path, thereby releasing the polypeptide of interest into the third fluid stream; and extracting the polypeptide of interest from the third fluid stream, wherein a polypeptide extract having at least 70% of the polypeptidered to the fementation slurry formed.

28. The method according to claim 27, wherein the amount of the polypeptide of interest released into the third fluid stream is greater than the amount of the polypeptide of interest released from the same cell by:

providing a slurry comprising the cell;

providing a shock buffer, wherein the osmolarity of the slurry is higher than the osmolarity of the shock buffer;

generating a first fluid stream comprising the slurry, wherein the first fluid stream has a first flow rate;

generating a second fluid stream comprising the shock buffer, wherein the second fluid stream has a second flow rate that is less than or approximately equal to the first flow rate; and non-continuously combining the first and second fluid streams, thereby releasing the polypeptide of interest into the third fluid stream.

* * * * *